US008672897B2

(12) United States Patent
Elahi et al.

(10) Patent No.: US 8,672,897 B2
(45) Date of Patent: Mar. 18, 2014

(54) MEDICAL DELIVERY SYSTEM COMPRISING LOCKING RING WITH L-SHAPED GROOVES

(75) Inventors: Ramin Nateghi Elahi, Gørløse (DK); Jonas Torry-Smith, Virum (DK); Michael Ejstrup Hansen, Morud (DK); Nikolaj Eusebius Jakobsen, Valby (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 12/447,757

(22) PCT Filed: Nov. 21, 2007

(86) PCT No.: PCT/EP2007/062661
§ 371 (c)(1),
(2), (4) Date: Apr. 1, 2010

(87) PCT Pub. No.: WO2008/062025
PCT Pub. Date: May 29, 2008

(65) Prior Publication Data
US 2011/0046566 A1    Feb. 24, 2011

Related U.S. Application Data

(60) Provisional application No. 60/873,079, filed on Dec. 6, 2006.

(30) Foreign Application Priority Data

Nov. 21, 2006    (EP) .................................... 06024098

(51) Int. Cl.
*A61M 5/00*    (2006.01)
*A61M 5/178*    (2006.01)

(52) U.S. Cl.
USPC ............................ 604/208; 604/211; 604/214

(58) Field of Classification Search
USPC ......................... 604/207–211, 218–231, 214
See application file for complete search history.

(56) References Cited

U.S. PATENT DOCUMENTS

RE31,873 E    4/1861    Cramer
RE31,878 E    4/1861    Downer
(Continued)

FOREIGN PATENT DOCUMENTS

CH    0315980    9/1956
CH    0501411    1/1971
(Continued)

OTHER PUBLICATIONS

English language translation for DE20110690.
(Continued)

*Primary Examiner* — Kami A Bosworth
*Assistant Examiner* — Imani Hayman
(74) *Attorney, Agent, or Firm* — Wesley A. Nicolas; Marc A. Began; Reza Green (57) ABSTRACT

A medical delivery system (100) comprising a container (102) which is adapted to be fastened to a dosing assembly (104). One of the container and the dosing assembly comprises a rotatable element (106) adapted to cooperate with the other one of the container and the dosing assembly, so as to lock/fasten the container to the dosing assembly. Furthermore, the present application relates to a container and a dosing assembly for use in the medical delivery system.

15 Claims, 4 Drawing Sheets

(56) References Cited

U.S. PATENT DOCUMENTS

| | | | |
|---|---|---|---|
| 1,594,493 A | 8/1926 | Brown |
| 2,020,828 A | 11/1935 | Goldberg |
| 2,392,196 A | 1/1946 | Smith |
| 2,707,466 A | 5/1955 | Hoskins |
| 2,818,864 A | 1/1958 | Hudson |
| 2,865,372 A | 12/1958 | Miskel et al. |
| 2,880,723 A | 4/1959 | Adams |
| 2,888,924 A | 6/1959 | Dunmire |
| 2,956,563 A | 10/1960 | Sarnoff |
| 3,021,840 A | 2/1962 | Hallamore et al. |
| 3,115,135 A | 12/1963 | Sarnoff |
| 3,130,724 A | 4/1964 | Higgins et al. |
| 3,130,742 A | 4/1964 | Higgins et al. |
| 3,144,178 A | 8/1964 | Sarnoff et al. |
| 3,170,667 A | 2/1965 | Szohatzky |
| 3,336,924 A | 8/1967 | Sarnoff et al. |
| 3,375,825 A | 4/1968 | Keller |
| 3,556,099 A | 1/1971 | Knight et al. |
| 3,820,652 A | 6/1974 | Thackston |
| 3,831,599 A | 8/1974 | Needham |
| 3,880,162 A | 4/1975 | Simmons |
| 3,895,633 A | 7/1975 | Bartner et al. |
| 3,916,893 A | 11/1975 | De Felice |
| 3,989,044 A | 11/1976 | Meierhoefer |
| 4,089,432 A | 5/1978 | Crankshaw |
| 4,150,673 A | 4/1979 | Watt |
| 4,280,723 A | 7/1981 | Moldestad |
| 4,314,556 A | 2/1982 | Ma |
| 4,490,142 A | 12/1984 | Silvern |
| 4,592,745 A | 6/1986 | Rex et al. |
| 4,619,640 A | 10/1986 | Potolsky et al. |
| 4,619,651 A | 10/1986 | Kopfer et al. |
| 4,664,656 A | 5/1987 | Taddei |
| 4,685,314 A | 8/1987 | Greenwalt et al. |
| 4,693,833 A | 9/1987 | Toshikuni et al. |
| 4,740,205 A | 4/1988 | Seltzer |
| 4,768,568 A | 9/1988 | Fournier et al. |
| 4,781,701 A | 11/1988 | Geprags |
| 4,944,736 A | 7/1990 | Holtz |
| 4,948,000 A | 8/1990 | Grabenkort |
| 4,973,318 A | 11/1990 | Holm et al. |
| 4,976,701 A | 12/1990 | Ejlersen et al. |
| 5,000,744 A | 3/1991 | Hoffman et al. |
| 5,002,537 A | 3/1991 | Hoffman et al. |
| 5,017,190 A | 5/1991 | Simon et al. |
| 5,078,698 A | 1/1992 | Stiehl et al. |
| 5,084,017 A | 1/1992 | Maffetone |
| 5,205,833 A | 4/1993 | Harsh et al. |
| 5,226,896 A | 7/1993 | Harris |
| 5,244,465 A | 9/1993 | Michel |
| 5,269,317 A | 12/1993 | Bennett |
| 5,286,258 A | 2/1994 | Haber et al. |
| 5,458,580 A | 10/1995 | Hajishoreh |
| 5,478,323 A | 12/1995 | Westwood et al. |
| 5,496,286 A | 3/1996 | Stiehl et al. |
| 5,498,253 A | 3/1996 | Aswad et al. |
| 5,554,134 A | 9/1996 | Bonnichsen |
| 5,584,815 A | 12/1996 | Pawelka et al. |
| 5,611,783 A | 3/1997 | Mikkelsen |
| 5,693,027 A | 12/1997 | Hansen et al. |
| 5,743,889 A | 4/1998 | Sams |
| 5,938,642 A | 8/1999 | Burroughs et al. |
| 5,954,700 A | 9/1999 | Kovelman |
| 5,957,896 A | 9/1999 | Bendek et al. |
| 6,017,330 A | 1/2000 | Hitchins et al. |
| 6,036,675 A | 3/2000 | Thorne et al. |
| 6,197,040 B1 | 3/2001 | LeVaughn et al. |
| 6,582,399 B1 | 6/2003 | Smith et al. |
| 6,582,408 B1 | 6/2003 | Buch-Rasmussen et al. |
| 6,648,859 B2 | 11/2003 | Bitdinger et al. |
| 6,752,798 B2 | 6/2004 | McWethy et al. |
| 7,604,619 B2 | 10/2009 | Eich et al. |
| 2001/0047153 A1 | 11/2001 | Trocki et al. |
| 2002/0016571 A1 | 2/2002 | Kirchhofer et al. |
| 2002/0099360 A1 | 7/2002 | Bierman |
| 2002/0169470 A1 | 11/2002 | Kuhr et al. |
| 2003/0004466 A1 | 1/2003 | Bitdinger et al. |
| 2003/0078195 A1 | 4/2003 | Kristensen et al. |
| 2004/0210199 A1 | 10/2004 | Atterbury |
| 2004/0215152 A1 | 10/2004 | Kirchhofer |
| 2004/0238776 A1 | 12/2004 | Peters et al. |
| 2006/0153693 A1 | 7/2006 | Fiechter et al. |
| 2008/0051713 A1 | 2/2008 | Kohlbrenner |
| 2010/0004603 A1 | 1/2010 | Kristensen et al. |
| 2010/0030158 A1* | 2/2010 | Christiansen ............ 604/208 |

FOREIGN PATENT DOCUMENTS

| | | |
|---|---|---|
| DE | 2137405 | 2/1973 |
| DE | 44 19 235 | 12/1995 |
| DE | 20110690 | 9/2001 |
| EP | 217055 | 4/1987 |
| EP | 0513128 | 11/1992 |
| EP | 549 694 | 7/1993 |
| EP | 762311 | 3/1997 |
| EP | 774270 | 5/1997 |
| EP | 832661 A2 | 4/1998 |
| EP | 897729 | 2/1999 |
| EP | 897728 | 5/2003 |
| GB | 301961 | 12/1928 |
| GB | 301961 A | 12/1928 |
| GB | 1205201 | 9/1970 |
| GB | 1437595 | 5/1976 |
| GB | 1525455 | 9/1978 |
| GB | 2 214 819 | 9/1989 |
| WO | WO89/02760 | 4/1989 |
| WO | WO 90/09202 | 8/1990 |
| WO | 9110460 | 7/1991 |
| WO | WO92/04926 | 4/1992 |
| WO | 9707841 | 3/1997 |
| WO | WO98/47559 | 10/1998 |
| WO | WO98/56438 | 12/1998 |
| WO | WO00/02605 | 1/2000 |
| WO | 00/35519 A1 | 6/2000 |
| WO | WO 00/35519 | 6/2000 |
| WO | WO 01/72361 | 10/2001 |
| WO | WO 02/30490 | 4/2002 |
| WO | WO 03/011372 | 2/2003 |
| WO | WO 03/011373 | 2/2003 |
| WO | WO03/017915 | 3/2003 |
| WO | 03097131 A1 | 11/2003 |
| WO | WO 2006/069456 | 7/2006 |
| WO | 2008/009646 A1 | 1/2008 |
| WO | WO 2008/009646 | 1/2008 |

OTHER PUBLICATIONS

English language translation for DE2137405.
English language translation for DE4419235.
English language translation for CH0315980.
English language translation for CH0501411.
Novo Nordisk Product Brochure for Insuject-X 1987.
Non-Final Office Action Mailed Apr. 9, 2004 in U.S. Appl. No. 10/230,428, filed Aug. 23, 2002; First Named Inventor: Kristensen.
Non-Final Office Action Mailed Nov. 18, 2004 in U.S. Appl. No. 10/230,428, filed Aug. 23, 2002; First Named Inventor: Kristensen.
Notice of Allowance Mailed May 19, 2005 in U.S. Appl. No. 10/230,428, filed Aug. 23, 2002; First Named Inventor: Krtstensen.
Non-Final Office Action Mailed Feb. 9, 2006 in U.S. Appl. No. 10/230,428, filed Aug. 23, 2002; First Named Inventor: Kristensen.
Notice of Allowance Mailed Oct. 10, 2006 in U.S. Appl. No. 10/230,428, filed Aug. 23, 2002; First Named Inventor: Kristensen.
Non-Final Office Action Mailed Dec. 12, 2006 in U.S. Appl. No. 10/230,428, filed Aug. 23, 2002; First Named Inventor: Kristensen.
Non-Final Office Action Mailed Feb. 10, 2009 in U.S. Appl. No. 11/784,738, filed Apr. 9, 2007; First Named Inventor Kristensen.
Final Office Action Mailed Jun. 2, 2009 in U.S. Appl. No. 11/784,738, filed Apr. 9, 2007; First Named Inventor Kristensen.
Final Office Action Mailed Aug. 12, 2010 in U.S. Appl. No. 12/522,566, filed Sep. 2, 2009; First Named Inventor: Kristensen.

(56) References Cited

OTHER PUBLICATIONS

Notice of Allowance Mailed Dec. 13, 2010 in U.S. Appl. No. 12/522,566, filed Sep. 2, 2009; First Named Inventor: Kristensen.
Non-Final Office Action Mailed Oct. 29, 2010 in U.S. Appl. No. 12/305,684, filed Dec. 19, 2008; First Named Inventor: Steenfeldt-Jensen.
Non-Final Office Action Mailed Jan. 19, 2010 in U.S. Appl. No. 12/373,339, filed Jan. 12, 2009 by Hansen.
Final Action Mailed Jul. 30, 2010 in U.S. Appl. No. 12/373,339, filed Jan. 12, 2009 by Hansen.
Non-Final Office Action Mailed Nov. 24, 2010 in U.S. Appl. No. 12/373,339, filed Jan.12, 2009 by Hansen.
Non-Final Office Action Mailed Feb. 18, 2011 in U.S. Appl. No. 12/373,340, filed January 12, 2009 by Christiansen.
Non-Final Office Action Mailed Feb. 17, 2011 in U.S. Appl. No. 12/357,013, filed Jan. 21, 2009 by Christiansen.
Non-Final Office Action Mailed Feb. 1, 2010 in U.S. Appl. No. 12/374,600, filed Jan. 21, 2009 by Christiansen.
Final Office Action Mailed Jul. 15, 2010 in U.S. Appl. No. 12/374,600, filed Jan. 21, 2009 by Christiansen.
Non-Final Office Action Mailed Mar. 4, 2011 in U.S. Appl. No. 12/374,600, filed Jan. 21, 2009 by Christiansen.
Search Report from International Application No. PCT/EP2007/062661, mailed Feb. 25, 2008.

* cited by examiner

MEDICAL DELIVERY SYSTEM COMPRISING LOCKING RING WITH L-SHAPED GROOVES

CROSS-REFERENCE TO RELATED APPLICATIONS

This application is a 35 U.S.C. §371 national stage application of International Patent Application PCT/EP2007/062661 (published as WO 2008/062025), filed Nov. 21, 2007, which claimed priority of European Patent Application 06024098.3, filed Nov. 21, 2006; this application further claims priority under 35 U.S.C. §119 of U.S. Provisional Application 60/873,079, filed Dec. 6, 2006.

FIELD OF THE INVENTION

The present invention relates to a medical delivery system comprising a container which is adapted to be fastened to a dosing assembly. In particular the present invention relates to a medical delivery system wherein one of the container and the dosing assembly comprises a rotatable element adapted to cooperate with the other one of the container and the dosing assembly. Furthermore, the present invention relates to a container and a dosing assembly for use in the medical delivery system.

BACKGROUND OF THE INVENTION

Generally, in order to provide superior medication delivery devices which are likely to be well received by particular groups of patients, a greater diversity in drug delivery systems have been launched to the benefit of patients. As the number of commercially available delivery systems increase, numerous different types of medication holding cartridges or containers are distributed. Most of these types of containers differ in various aspects.

Each medicament container may be filled with a particular type of medicament selected from a large variety of different medicaments, but also different kinds of the same class of medicament (e.g. rapid or long acting insulin) and different concentrations of each particular medicament may be accommodated in the containers.

Moreover, different container volumes may be introduced in order to customize each container, and, thus, the delivery system to the needs of particular users. Variation of container volume may be provided by changing the length or diameter of the container. These modifications usually imply corresponding modifications of the dosing assembly of a medication delivery system, so as to provide a particular stroke of a driving element for expelling the medicament from the container or to provide optimal dosing precision. Further discrimination between different medicament containers may be occasioned by the design requirements for each particular delivery system, such as required sliding friction of the piston accommodated in the container.

In order to discriminate between a larger variety of available containers, numerous container coding and coupling systems have been developed. The following mechanical coding and coupling systems are known in the art:

U.S. Pat. No. 5,611,783 relates to a pen shaped syringe comprising a distal part which may comprise an ampoule and a proximal part containing a dose setting and drive mechanism. The proximal and distal parts have interlocking bayonet coupling means. Protrusions may be provided to form a pattern ensuring that a certain distal part may only be used in connection with a certain proximal part.

WO 03/017915 A1 discloses a cartridge having a distal end provided with a mechanical coding. The mechanical coding has the form of a circular protrusion where the circular outer diameter is dedicated a specific concentration of insulin contained in the cartridge.

U.S. Pat. No. 5,693,027 discloses a plastic top for adapting a standard cartridge to a chosen syringe. The plastic top may be provided with means for keyed engagement with corresponding means in a syringe to keep it unrotable when mounted with a cartridge in the syringe. In some types of syringes such keyed engagement between cartridge and syringe is further used to ensure that only a certain type of cartridge is used.

U.S. Pat. No. 6,648,859 B2 discloses a drug cartridge assembly for use with a reusable pen body assembly of a medication delivery pen. In order to eliminate cross-use the pen body assembly and the drug cartridge are keyed i.e. they may be threadedly engaged by corresponding threads and grooves, bayonet threads, and grooves, snap fits or a pair of lugs that mate in reverse Luer-Lock manner. The mating members are selected so as to prevent cross-use with other assemblies, e.g., the pitch of the threads may be angled so as to mate only with one another and not with other assemblies.

Yet another prior art system is described in DE 201 10 690.

GB patent No. 301,961 discloses a syringe wherein a barrel member holding an ampule is provided with a radially extending pin which is cooperating with a bayonet slot formed in a head. The head is attached to the barrel by a conventional bayonet coupling movement including a relative rotational movement between barrel and head.

It is an object of a preferred embodiment of the present invention to provide an alternative to the known systems. Furthermore, it is an object of a preferred embodiment of the present invention to provide a medication delivery system with a large number of possible coding geometries, while obtaining a robust coding system.

Furthermore, it is an object of a preferred embodiment of the present invention to provide a coding system wherein the user experiences substantially the same operational fastening/coupling/locking movement when the container and dosing assembly of a predetermined medical delivery system are coupled/uncoupled (locked/unlocked) to each other regardless of the specific choice among sets of compatible container/dosing assemblies.

Furthermore, it is an object of a preferred embodiment of the present invention to provide an intuitive and simple fastening mechanism for fastening the container to the dosing assembly.

Moreover, it is an object of the present invention to provide a locking/fastening system wherein the user experiences an auditive or tactile feed back when locking the container to the dosing assembly.

SUMMARY OF THE INVENTION

In a FIRST aspect the present invention relates to a medical delivery system comprising:
- a container adapted to contain a medicament in a chamber defined by the container and a slidably arranged piston which is moveable in a distal direction towards an outlet so as to reduce the volume of the chamber and expel the medicament through the outlet;
- a dosing assembly adapted to be fastened to the container, so as to allow a driver of the dosing assembly to move the piston of the container in the distal direction;

wherein one of the dosing assembly and the container defines a first part comprising a fixed part and a rotatable element defining one or more projection(s) and/or groove(s) which during fastening of the container to the dosing assembly is/are adapted to be received in/by one or more corresponding groove(s) and/or projection(s) of a second part which is defined by the other one of the dosing assembly and the container, so as to fasten the container to the dosing assembly; and wherein the rotatable element is adapted to rotate about a longitudinal axis of and relative to the container and/or the dosing assembly during fastening of the container to the dosing assembly.

The container and the dosing assembly may be locked rotationally to each other during fastening of the container to the dosing assembly. In one embodiment, only a part of the container and only a part of the dosing assembly are locked rotationally relative to each other during fastening of the container to the dosing assembly. In another embodiment the first part except from the rotatable element and the second part are locked relative to each other during fastening of the container to the dosing assembly. The rotational lock may be achieved by providing a grove and tongue arrangement on the two parts to be locked rotationally. Alternatively, or as a supplement the two parts may each have a cross-section preventing relative rotation, e.g. the container may have an elliptical cross-section and the dosing assembly may define a corresponding elliptical cavity for receiving the container. By providing the rotational lock, fastening of the container to the dosing assembly is easy and intuitive for the user, as the container is fastened to the dosing assembly through a pure or substantially pure translational movement.

By varying the rotational distribution and/or geometrical dimensions of the projections/grooves formed in the rotatable element and the corresponding part of the other of the dosing assembly/container not holding the rotatable element in different medical delivery systems according to the present invention, it may be ensured that a container of a first medical delivery system is coded such that it cannot be fastened to a dosing assembly of a second medical delivery system. Analogously, it may be ensured that the container of the second medical delivery system is coded such that it cannot be fastened to the dosing assembly of the first medical delivery system. Accordingly, the medical system according to the present invention improves user safety as only predetermined containers may be attached to a specific dosing assembly. Thus, the dosing assembly may be designated to be used with a predetermined kind and/or concentration of a medicament and containers accommodating other concentrations or types of medicaments cannot be attached to the dosing assembly. Furthermore, by ensuring that the container and the dosing assembly (with the exception of the rotational element) is locked rotationally to each other during fastening of the container to the dosing assembly, it is ensured that a large number of distinct codings can be obtained.

In the context of the present invention the term "medical delivery system" shall be understood as any system capable of administering a medicament-containing flowable drug. Examples of medical delivery systems are infusion pump applications, dosers, pen-shaped dosers, motor-dosers, and automated syringes such as the AutoPen™.

The invention is applicable to all kinds of medicament delivery devices capable of delivering a medicament to a user from a container which is adapted to be coupled to a dosing assembly of the delivery device. The delivery device may include any delivery device for transcutaneous, subcutaneous, intravenous, intra muscular or pulmonary administration of a drug.

As used herein, the term "medicament" is meant to encompass any medicament-containing flowable drug capable of being passed through a delivery means such as a hollow needle in a controlled manner, such as a liquid, solution, gel or fine suspension. Representative medicaments includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

The chamber of the container may defined by one or more sidewalls of the container and the slidably arranged piston. In most embodiments at least a part of the container is ring-shaped (having a cylindrical cross-section) and defines a cylindrical cavity in which the piston is received. The distal end of the container may comprise a seal for penetration by a cannula so as to allow a medicament contained in the chamber to be expelled through the cannula. The distal end of the container may be adapted to be attached to a holder holding a cannula. As an example the distal end of the container may comprise a thread adapted to cooperate with a corresponding thread of the holder so as to allow the holder to be screwed onto the container.

The outlet of the container may be adapted to cooperate with or be defined by a cannula or a needle or a needle hub or an infusion set, or any other fluid communicating conduit adapted to provide fluid access to a medicament accommodated in the container.

The driver of the dosing assembly may comprise a piston rod adapted to move the piston in the distal direction. The piston rod may comprise an element which is more rigid than the piston and is adapted to abut at least a part of and preferably most of the proximal facing surface of the piston whereby a force applied by the piston rod to the rigid element is applied to a larger area of the proximal surface of the piston than if the piston rod had engaged the piston directly.

The rotatable element may be ring-shaped and may in use encircle at least a part of the dosing assembly and/or the container. Alternatively, the rotatable element may encircle only a part of the container and/or the container.

In the context of the present invention the term "remainder of the first part" shall designate the first part except from the rotatable element. In some embodiments, the remainder of the first part may form a housing structure which is adapted to be gripped by the palm of the user. In that case, preferably, the rotatable element defines an exterior surface which is comparatively smaller than the remainder of the first part.

In one embodiment the rotatable element defines one or more projections (such as two, three, four or five) each of which is adapted to engage a corresponding/mating/matching depression of the second part. In a second embodiment the rotatable element defines one or more grooves (such as two, three, four or five) each of which is adapted to engage a corresponding/mating/matching projection of the second part. In a third embodiment the rotatable element comprises one or more projections and one or more grooves. In the latter embodiment, the projection(s) of the rotatable element is/are adapted to engage one or more grooves of the second part and the groove(s) is/are adapted to engage one or more projections of the second part.

In order to ensure that the container and the dosing assembly may be locked to each other translationally, the one or more projection(s) and/or groove(s) of the rotatable element may engage the one or more groove(s) and/or projection(s) of the second part during fastening of the container to the dosing assembly. In one embodiment the container and the dosing assembly are locked for relative translational movement in one direction when the projection(s) engage the grove(s), whereby the container and the dosing assembly may be moved further towards each other but not away from each other. In another embodiment the container and the dosing assembly are locked for relative translational movement in both translational directions when the projection(s) engage the groove(s) whereby they cannot be moved further towards or away from each other.

Advancement of the projection(s) into the groove(s) during fastening of the container to the dosing assembly, may cause the rotatable element to rotate about the longitudinal axis of and relative to the container and/or the dosing assembly. In one embodiment this is achieved by providing one or more projections on the container and a corresponding number of grooves on the rotatable element. In order to make the rotatable element rotate during fastening of the container to the dosing assembly, at least a part of the groove may extent in a direction transverse to the longitudinal direction of the device. Examples of grooves causing the rotatable element to rotate are L-shaped, V-shaped and S-shaped grooves.

In most embodiments wherein fastening of the container to the dosing assembly causes the rotatable element to rotate, the rotatable element will also rotate during defastening/decoupling/unlocking of the container from the dosing assembly. Accordingly, locking of the rotatable element rotationally relative to the remainder of the first part prevents unlocking of the container from the dosing assembly. The device may in one embodiment comprise such a lock for locking the rotatable element relative to the container and/or the dosing assembly. When a container is not fastened to the dosing assembly, activation of the lock prevents fastening of a container to the dosing assembly. When, as described above, a container is fastened to the dosing assembly, activation of the lock prevents defastening/decoupling/unlocking of the container from the dosing assembly.

It will be appreciated that the shape of the groove(s) determines the degree of rotation of the rotatable element. In one embodiment the groove(s) is/are shaped such that the rotatable element during fastening is rotated less than one revolution relative to the container and/or the dosing assembly, such as less than 180 degrees, such as less than 120 degrees, such as less than 90 degrees, such as less than 60 degrees, such as less than 45 degrees, such as less than 30 degrees, such as less than 15 degrees.

Moreover, the groove(s) of the first and/or second part may be shaped such that advancement of the corresponding projection into the groove during fastening of the container to the dosing assembly, causes the rotatable element to rotate in a first direction and subsequently in a opposite second direction relative to the first and/or second part. When advanced in the first direction the rotatable element may be rotated X degrees, and when rotated in the second direction the rotatable element may be rotated Y degrees. The numerical value of X and Y may be identical e.g. when X=30 degrees and Y=−30 degrees, whereby X+Y=0. Alternatively, X+Y may be different from zero, such as ±5 degrees, such as ±10 degrees, such as ±15 degrees, such as ±20 degrees. When X+Y≠0, the rotational element is rotated more in one of the first and second direction than in the other one of the first and second direction. As an example the rotatable element may be rotated 30 degrees in the first direction and subsequently 20 degrees in the second direction during fastening of the container to the dosing assembly.

At least one of the grooves of the first and/or second part may define a first and a second groove part. The first and second groove parts may be shaped such that advancement of a corresponding projection into said groove parts causes the rotatable element to rotate in the first direction when the projection, during fastening, is advanced in the first groove part and in the second direction when the projection, during fastening, is advanced in the second groove part. In one embodiment at least one of the first and second groove parts is substantially straight and the first and second groove parts are interconnected by an interconnecting groove part. In one embodiment a general direction of the second groove part may extend in a direction transverse to the axial direction of the medical delivery system and at an angle of larger than 70 degrees to said axial direction, such as above 80 degrees.

In one embodiment the rotatable element may rotate freely relative to the remainder of the first part and/or relative to the second part. However, in most embodiments the rotatable element is adapted to be rotated between a first position and a second position relative to the container and/or the dosing assembly (i.e. relative to the remainder of the first part and/or the second part). Moreover, the rotatable element may be biased towards the first position. In order to bias the rotatable element towards the first position, the first part may comprise a biasing means arranged to bias the rotatable element towards the first position. The biasing means may comprise a torsion spring having a first end fastened to the rotatable element and a second end fastened to the remainder of the first part. Alternatively, the biasing means may comprise flat spring retained relative by the remainder of the first part and extending into a cavity of the rotatable element such that rotation of the rotatable element causes the flat spring to be bend whereby the rotational element is urged towards the first position. It will be appreciated, that the flat spring need not be flat as long at it has a large axial extent relative to the thickness of the spring and as long as it is bendable.

In one embodiment advancement of the projection in the first groove part during fastening of the container to the dosing assembly, causes the rotatable element to be rotated away from the first position. Moreover, advancement of said projection in the second groove part during fastening of the container to the dosing assembly, may cause the rotatable element to be rotated back towards the first position. When the projection during fastening is advanced in the first groove part and the rotatable element is forced away from the first position, potential energy may be stored/accumulated in/by the spring. Additionally, potential energy stored in the spring may be released/dispensed when the projection during fastening is advanced in the second groove part.

In one embodiment the second groove part is steeper than the first groove part relative to the axial direction of the medical delivery system. In the context of the present invention the term "steeper" shall be understood such that the steepness of a surface, plane etc. increases the closer the surface, plane etc is to define a right angle relative to reference such as an axial direction of the medical delivery system. In one embodiment a plane extending in a general direction of the second groove part defines an angle relative to the axial direction of the medical delivery system which is above 70 degrees. It will be appreciated that a spring-biased rotational element with a steep second groove part e.g. above 70 degrees, must be rotated by a user in order to allow the container to disengage the dosing assembly. Moreover, it will be appreciated that the steeper the second groove part is the harder it is for the container to disengage the dosing assembly by accident, as the spring urges the projections towards the bottom of the second groove, whereby the projections cannot move from the second groove part to the first groove part.

In one embodiment the one or more of the projections and/or the grooves define predetermined coding geometries preventing the container from being fastened to the dosing assembly unless each of the grooves and the projections define a predetermined coding geometry which may be selected from a predetermined group of coding geometries. The coding geometry of each of the grooves and/or projections may be defined by at least one of: a circumferential extent of the groove(s) and/or the projection(s), an axial extent of the groove(s) and/or the projection(s), a radial extent of the groove(s) and/or the projection(s) and the circumferential position of the groove(s) and/or the projection(s).

One embodiment comprises:
  a first container according to any of the preceding claims adapted to be fastened to a first dosing assembly according to any of the preceding claims; and
  a second container according to any of the preceding claims adapted to be fastened to a second dosing assembly according to any of the preceding claims; and
wherein at least one of the groove(s) and the projection(s) is adapted to prevent the first dosing assembly and second container from being fastened to each other, and to prevent the second dosing assembly and the first container from being fastened to each other.

In one embodiment the container comprises a cartridge holder which is adapted to accommodate a cartridge defining said chamber. The second fastening means may be defined by or attached to the cartridge holder. Moreover, the groove(s)/projection(s) may be defined by the cartridge holder. When the cartridge and the cartridge holder are two distinct elements, the cartridge may be frictionally retained in the cartridge holder. In one embodiment the cartridge is made of glass and the cartridge holder is made of a non-glass material for protecting the glass cartridge. The cartridge may be non-removably retained in the cartridge holder, such that if the cartridge is removed from the cartridge holder it cannot be reattached by hand and without tools. This provides the advantage that the cartridge holder cannot be reused when the cartridge has been emptied, accordingly a cartridge with a wrong medicament cannot be inserted into the cartridge holder and be dispensed by use of the dosing assembly. The cartridge holder and the cartridge may define a monolithic element, i.e. forming a one element without seams. Such a monolithic element may be formed as a molded article made of a synthetic resin such as Topas® or polypropylene. Such a molded article may include the fastening and coding geometries which are formed during molding. However, any material which is suitable for long-term storage of the specific medication to be accommodated in the container may be used.

In a SECOND aspect the present invention relates to a container for use in a medical delivery system according to the first aspect of the invention. The invention according to the second aspect may comprise any feature and/or element of the invention according to the first aspect. As an example the container may be adapted to contain a medicament in a chamber defined by the container and a slidably arranged piston which is movable in a distal direction towards an outlet so as to reduce the volume of the chamber and expel the medicament. In one embodiment, the container may comprise a rotatable element adapted to rotate about a longitudinal axis of and relative to the remainder of the container. The rotatable element define one or more projection(s) and/or groove(s). The one or more projection(s) and/or groove(s) of the rotatable element may be adapted to receive one or more corresponding groove(s) and/or projection(s) of a dosing assembly, so as to fasten the container to the dosing assembly. The container may provide, on the remainder of the container as defined above, one or more projections and/or grooves adapted to cooperate with mating projections or grooves formed in the dosing assembly, so as to provide a rotational lock between the dosing assembly and the remainder of the container. The rotational lock may form an axially extending guide ensuring rotationally fixation of the remainder of the container with respect to the dosing assembly during complete or part of the fastening procedure.

In a THIRD aspect the present invention relates to dosing assembly suitable for use in a medical delivery system according to the first aspect of the invention. The invention according to the third aspect may comprise any feature and/or element of the invention according to the first aspect. Also, the invention according to the third aspect may be formed to cooperate with a container assembly according to the second aspect of the invention.

DETAILED DESCRIPTION OF THE DRAWINGS

FIGS. 1-4 disclose a medical delivery system 100 according to a first embodiment. The system 100 comprises a container 102 and a dosing assembly 104, which for simplicity reasons, is not shown in its entirety. However, it will be appreciated that the dosing assembly 104 may also comprise a dose setting mechanism and an injection mechanism. Moreover, the system 100 comprises a rotatable element 106, which is made of an outer part 108 visible in FIG. 1 and an inner part 110 visible in FIG. 2. The inner part 110 and the outer part 108 may be fastened to each other through a snap-lock, gluing or welding or by any other means of fastening which causes rotation of the outer part 108 to be transferred to the inner part 110 when the two parts are fastened to each other. In an embodiment the inner and outer parts 110,108 define a monolithic element i.e. made in one piece without seams.

Figure 1:
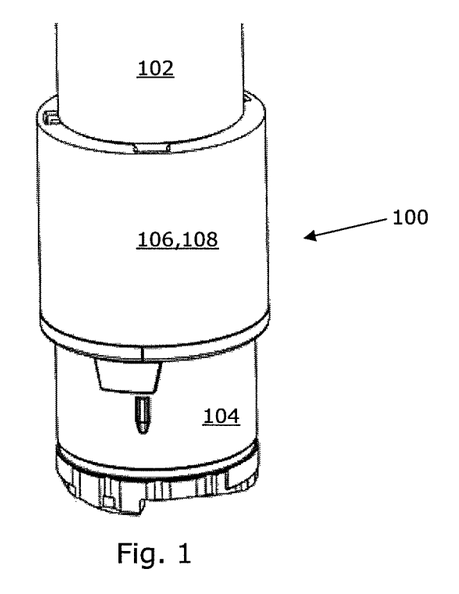
FIGS. 1 and 2 disclose a medical delivery system according to a first embodiment, FIG. 3 discloses a sectional view in the longitudinal direction of the system according to the first embodiment, FIG. 4 discloses an exploded view of a system according to the first embodiment, and FIG. 5 discloses a medical delivery system according to a second embodiment.
Figure 2:
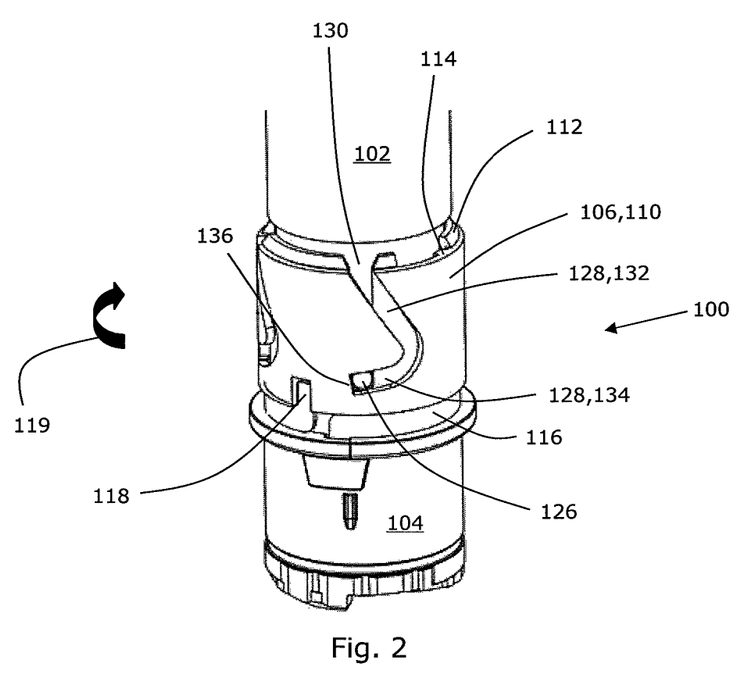

The rotatable element 106 is retained axially relative to the dosing assembly 104 due to snap locks 112, which engage a distal facing surface 114 of the rotatable element 106. In the axially retained position the rotatable element 106 may rotate relative to the dosing assembly 104 between a first and a second position. In FIG. 2 the rotatable element 106 is shown in the first position towards which the rotatable element 106 is biased due to torsion spring 116. The torsion spring 116 comprises a distal tap 118 and a proximal tap 120 visible in FIG. 4 which engage indentations of the rotatable element 106 and the dosing assembly 104, respectively. Accordingly, rotation or the rotatable element 106 in a first rotational direction 119 relative to the dosing assembly 104 causes the spring 116 to expand. When the rotatable element 106 is positioned in the first position, the spring 116 is in a rest position whereas when the rotatable element 106 is in the second position the spring 116 is in a non-rest position wherein potential energy is stored in the spring 116, and the spring 116 urges the rotatable element 106 towards the rest position of FIG. 2.

Figure 4:
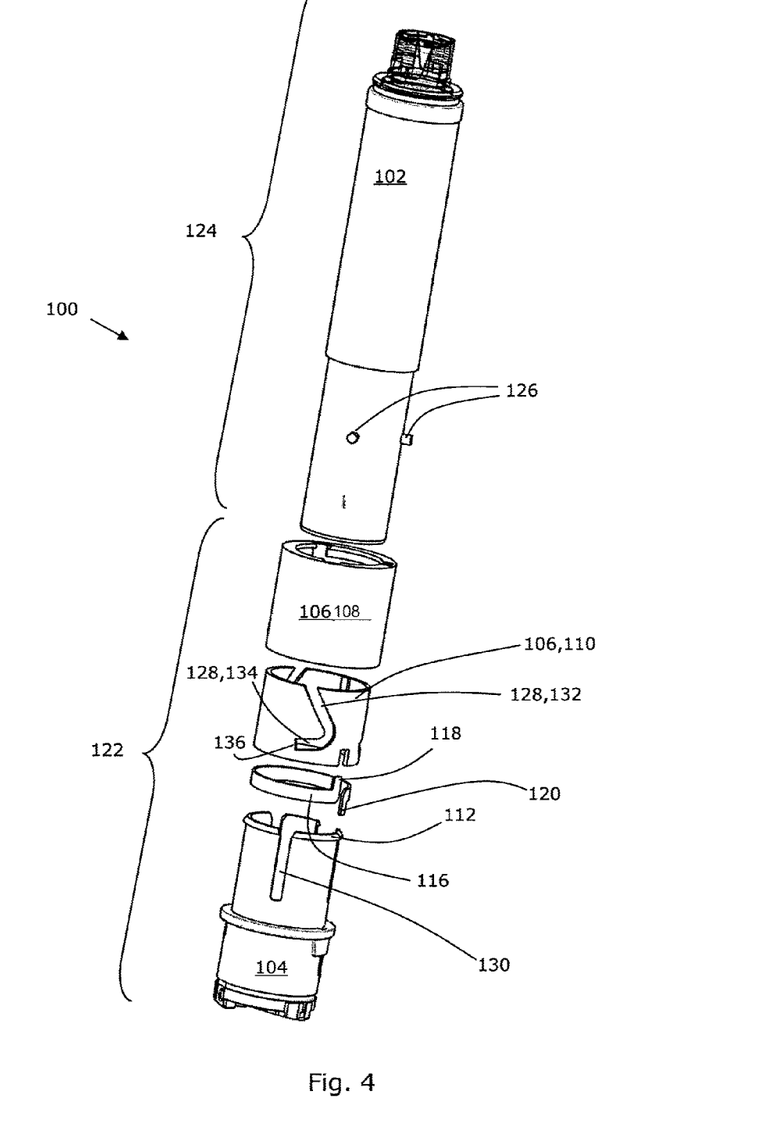

The rotatable element 106, the torsion spring 116 and the dosing assembly 104 define a first part 122 and the container 102 defines a second part 124, see FIG. 4. The container 102 defines three projections 126 each of which is adapted to engage corresponding L-shaped grooves 128 of the rotatable element 106 during insertion of the container 102 into the dosing assembly 104. Moreover, the dosing assembly defines linear grooves 130 which the projections 126 additionally engage during insertion of the container 102 into the dosing assembly 104, whereby the container 102 is rotationally fixed relative to the dosing assembly 104.

Due to the rotational lock caused by the groove-tongue engagement between the projections 126 and the linear grooves 130, translational movement of the projections 126 towards the dosing assembly 104 causes the rotatable element 106 to rotate as the projections 126 are advanced into the L-shaped grooves 128. As the L-shaped grooves comprises a first groove part 132 and second groove part 134, the rotatable element will initially rotate in the first rotational direction 119 when the projections 126 are advanced translationally in the first groove part 132 and subsequently in a direction opposite the first rotational direction 119, when the projections 126 are advanced translationally in the second groove parts 134.

In FIG. 2 the second groove part 134 is steeper than the first groove part 132, relative to the axial direction of the device. In the present context, the term "steeper" shall be understood such that the steepness of a surface, plane etc. increases the closer the surface, plane etc is to define a right angle relative to reference in this case the axial direction of the medical delivery system. It will be appreciated that the steeper the groove parts 132,134 are, the larger the angular rotation of the rotatable element will be, when the projections are moved a predetermined axial distance relative to the rotatable element 106 and/or the dosing assembly 104.

In a special embodiment the second groove part 134 is substantially at right angle relative to the axial direction of the device, and thus advancement of the projection 126 from the first groove part 132 into the second groove part 134 causes the rotatable element to be moved rapidly into the first position due to the torsion spring 116. When the rapid movement is terminated due to a bottom surface 136 (see FIG. 4) of the second groove part 134 being forced towards a surface of the projection 126 (as shown in FIG. 2), the user is provided with audio/tactile information indicating that the container 102 is properly fastened to the dosing assembly 104.

Moreover it will be appreciated that the steeper the second groove part 134 is, the better the container 102 is secured to the dosing assembly 104. As the rotatable element is forced towards the first position as disclosed in FIG. 2, the user must rotate the rotatable element away from the first position (against the force of the spring 116) in order to allow the projections to be moved from the second groove part 134 into the first groove part 132.

Figure 3:
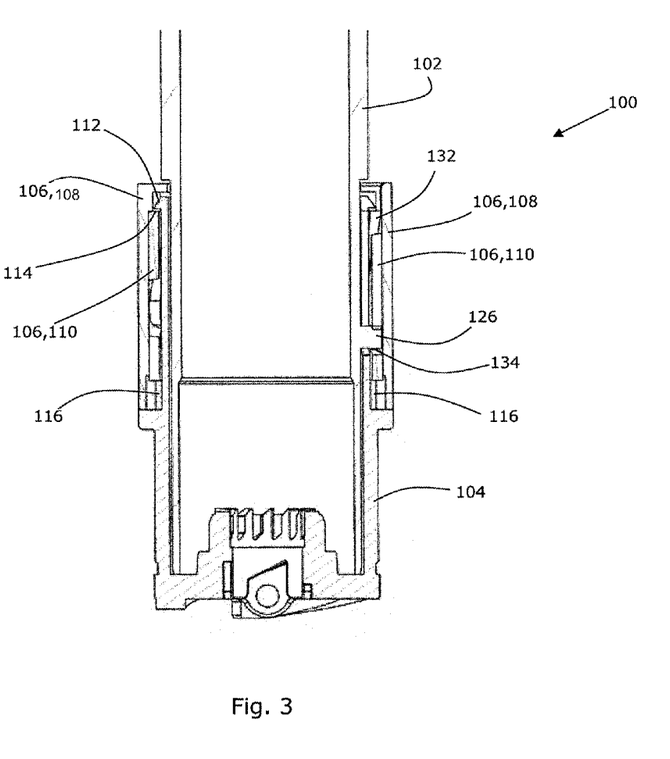

FIG. 3 discloses a section of the medical delivery system 100 according to the first embodiment, and discloses the container 102, the dosing assembly 104 and the rotatable element 106 which is comprises an outer part 108 and an inner part 110. The rotatable element 106 is retained axially relative to the dosing assembly 104 due to engagement between snap lock 112 and distal facing surface 114 of the rotatable element 106. The inner part 110 defines a first groove part 132 and a second groove part 134, in which the projection 126 is positioned in FIG. 3. As described above, the spring 116 urges the rotational element 106 towards a first position relative to the dosing assembly 104. FIG. 4 discloses an exploded view of the medical delivery system 100 according to the first embodiment reference numbers identical to the reference numbers of the previous figures refer to identical features.

Figure 5:
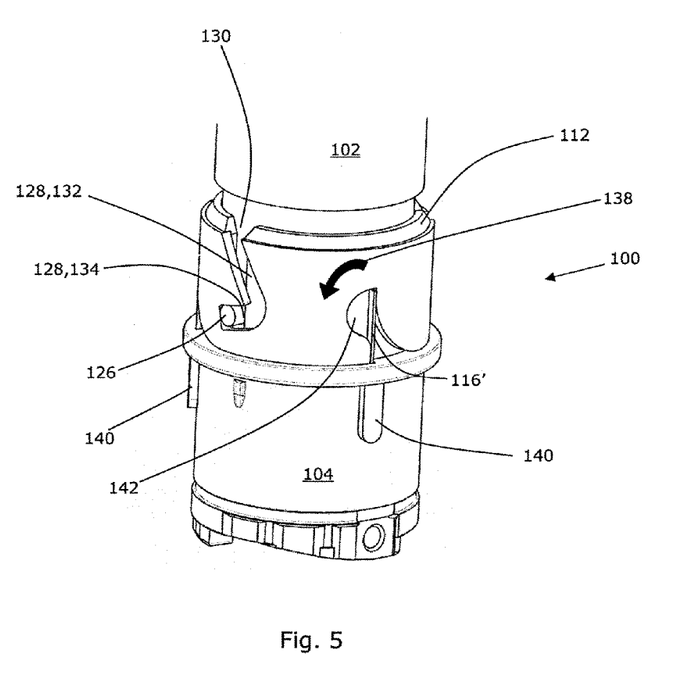

FIG. 5 discloses a second embodiment of the medical delivery system 100. The main difference is the spring 116' which in the second embodiment a linearly extending spring and not a torsion spring. The advantage of the linearly extending spring 116' is that it does not expand radially when the rotational element 106 is rotated relative to the dosing assembly 104. Instead the spring is bent in the direction indicated by arrow 138. The spring is retained in a passage defined in the housing 140 and extends into a groove 142 defined in the rotatable element 106.

In the embodiments shown, the rotatable element 106 is configured to fully or partly encircle the distal end of the container. Other embodiments may include a dosing assembly 104 having a rotatable element 106 configured to be inserted into a distal opening formed in the distal end face of the container, whereby the mating grooves and projections engage internally in said distal opening. In such an embodiment, projections may be formed on an internal wall section of the container so that the projections extends radially inwards. In this case, a mechanism in the dosing assembly may be provided such that a manually actuatable member, accessible from the exterior of the dosing assembly, is configured to rotate the rotatable element 106 so as to release the container from the dosing assembly.

In the embodiments shown, the container is rotationally locked relative to the dosing assembly during insertion and coupling due to the projections 126 engaging the linear grooves 130 formed in the dosing assembly 104, i.e. the linear grooves 130 defines an axially extending guide for the projections.

However, any other means may be provided for establishing a rotational lock for rotatively fixing the container relative to the dosing assembly when the container is engaged to the dosing assembly. For example, the container may provide a projection formed on an interior proximal wall section of the container which is configured to engage a corresponding recessed area formed in the dosing assembly so that the container, when coupled to the dosing assembly, is rotationally fixed relative to the dosing assembly. In an alternative embodiment, a container having a proximal end face is provided, where the end face is provided with axially recessed areas that engages corresponding axially extending protrusions formed in the dosing assembly.

As shown in the fist and second embodiment, the rotational lock may form an axially extending guide which provides rotationally fixation during a substantial part of axial movement during coupling and uncoupling of the container to the dosing assembly. However, in alternative embodiments, the rotational lock may provide a rotationally fixation only during the final stage of axially engaging the container to the dosing assembly.

The invention claimed is:

1. A medical delivery system comprising:
   a container adapted to contain a medicament in a chamber defined by the container and a slidably arranged piston which is moveable in a distal direction towards an outlet so as to reduce a volume of the chamber and expel the medicament through the outlet;
   a dosing assembly adapted to be fastened to the container, so as to allow a driver of the dosing assembly to move the slidably arranged piston of the container in the distal direction;
     wherein one of the dosing assembly and the container defines a first part comprising a fixed part and a rotatable element rotatably mounted relative to the fixed part, the rotatable element defining at least one projection and/or groove which during fastening of the container to the dosing assembly is adapted to be received in/by at least one corresponding groove and/or projection of a second part which is defined by the other one of the dosing assembly and the container, so as to fasten the container to the dosing assembly; and wherein during fastening of the container to the dosing assembly the rotatable element is adapted to rotate about a longitudinal axis of and relative to said fixed part, and wherein said fixed part and the second part comprise engaging surfaces configured for rotationally locking said fixed part relative to the second part so that during fastening the second part and the fixed part do not rotate relative to one another.

2. A medical delivery system according to claim 1, wherein during fastening of the container to the dosing assembly, the at least one projection and/or groove of the rotatable element engages the at least one groove and/or projection of the second part such that the container is locked for translational movement relative to the dosing assembly.

3. A medical delivery system according to claim 1, wherein advancement of the at least one projection into the corresponding groove during fastening of the container to the dosing assembly, causes the rotatable element to rotate about the axis of and relative to the container and/or the dosing assembly.

4. A medical delivery system according to claim 1, wherein the rotatable element during fastening, is adapted to be rotated less than one revolution relative to the fixed part.

5. A medical delivery system according to claim 1, wherein at least one groove of the first and/or second part is/are shaped such that advancement of the corresponding projection into the groove during fastening of the container to the dosing assembly, causes the rotatable element to rotate in a first direction and subsequently in an opposite second direction relative to the first and/or second part.

6. A medical delivery system according to claim 5, wherein the at least one groove of the first and/or second part defines a first and a second groove part, and wherein advancement of a corresponding projection into said groove parts causes the rotatable element to rotate in the first direction when the projection, during fastening, is advanced in the first groove part and in the second direction when the projection, during fastening, is advanced in the second groove part.

7. A medical delivery system according to claim 6, wherein advancement of the at least one projection in the first groove part during fastening of the container to the dosing assembly causes the rotatable element to be rotated away from the first position and wherein advancement of a projection in the second groove part during fastening of the container to the dosing assembly, causes the rotatable element to be rotated back towards the first position.

8. A medical delivery system according to claim 6, wherein the second groove part is steeper than the first groove part relative to the axial direction of the medical delivery system.

9. A medical delivery system according to claim 6, wherein a plane extending in a general direction of the second groove part defines an angle relative to the axial direction of the medical delivery system which is above 70 degrees.

10. A medical delivery system according to claim 1, wherein the rotatable element is adapted to be rotated between a first position and a second position relative to the container and/or the dosing assembly and wherein the rotatable element is biased towards the first position.

11. A medical delivery system according to claim 1, wherein the at least one projection and/or the groove define predetermined coding geometries preventing the container from being fastened to the dosing assembly unless each of the grooves and the projections define a predetermined coding geometry which is selected from a predetermined group of coding geometries.

12. A medical delivery system according to claim 11, wherein the coding geometry of the at least one groove and/or projection is defined by at least one of: a circumferential extent of the groove and/or the projection, an axial extent of the groove and/or the projection, a radial extent of the groove and/or the projection and the circumferential position of the groove and/or the projection.

13. A medical delivery system according to claim 1, comprising:

a first container adapted to be fastened to a first dosing assembly; and a second container adapted to be fastened to a second dosing assembly; and wherein the at least one groove and the at least one projection is adapted to prevent the first dosing assembly and second container from being fastened to each other, and to prevent the second dosing assembly and the first container from being fastened to each other.

14. A medical delivery system according to claim 1, wherein during engagement of the container to the dosing assembly, the rotational element is not fixed rotationally with respect to the second part.

15. A medical delivery system comprising:

a container adapted to contain a medicament in a chamber defined by the container and a slidably arranged piston which is moveable in a distal direction towards an outlet so as to reduce a volume of the chamber and expel the medicament through the outlet;

a dosing assembly adapted to be fastened to the container, so as to allow a driver of the dosing assembly to move the slidably arranged piston of the container in the distal direction;

wherein one of the dosing assembly and the container defines a first part having at least one projection and/or groove which during fastening of the container to the dosing assembly is adapted to be received in/by at least one corresponding groove and/or projection of a second part which is defined by the other one of the dosing assembly and the container, so as to fasten the container to the dosing assembly; and wherein the first part comprises a fixed part and a rotatable element rotatably mounted relative to the fixed part, the rotatable element defining said at least one projection and/or groove which during fastening of the container to the dosing assembly is adapted to be received in/by said at least one corresponding groove and/or projection of said second part, and wherein the rotatable element is adapted to rotate about a longitudinal axis of and relative to said fixed part during fastening of the container to the dosing assembly and wherein said fixed part and the second part comprise engaging surfaces configured for rotationally locking said fixed part to the second part, wherein at least one groove of the first and/or second part is/are shaped such that advancement of the corresponding projection into the groove during fastening of the container to the dosing assembly, causes the rotatable element to rotate in a first direction and subsequently in an opposite second direction relative to the first and/or second part.

* * * * *

UNITED STATES PATENT AND TRADEMARK OFFICE
CERTIFICATE OF CORRECTION

| | | |
|---|---|---|
| PATENT NO. | : 8,672,897 B2 | Page 1 of 1 |
| APPLICATION NO. | : 12/447757 | |
| DATED | : March 18, 2014 | |
| INVENTOR(S) | : Elahi et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 476 days.

Signed and Sealed this
Twenty-first Day of July, 2015

Michelle K. Lee
*Director of the United States Patent and Trademark Office*